(12) United States Patent
Schmid et al.

(10) Patent No.: US 9,283,309 B2
(45) Date of Patent: Mar. 15, 2016

(54) DEVICE FOR SUPPLYING ENERGY TO HYDRAULICALLY OR PNEUMATICALLY ACTUATED ACTIVE IMPLANTS

(75) Inventors: Thomas Schmid, Herrsching (DE);
Bernhard Vodermayer, Gilching (DE);
Cornelia Riecke, Germering (DE);
Annika Rybak, Neuried (DE); Matthias Grzeski, München (DE)

(73) Assignee: Deutsches Zentrum Fuer Luft-Und Raumfahrt E.V., Cologne (DE)

( * ) Notice: Subject to any disclaimer, the term of this patent is extended or adjusted under 35 U.S.C. 154(b) by 418 days.

(21) Appl. No.: 13/635,806

(22) PCT Filed: Mar. 18, 2011

(86) PCT No.: PCT/EP2011/054131
§ 371 (c)(1),
(2), (4) Date: Sep. 18, 2012

(87) PCT Pub. No.: WO2011/113934
PCT Pub. Date: Sep. 22, 2011

(65) Prior Publication Data
US 2013/0053980 A1 Feb. 28, 2013

(30) Foreign Application Priority Data
Mar. 18, 2010 (DE) .......................... 10 2010 011 940

(51) Int. Cl.
*A61M 1/12* (2006.01)
*A61M 1/10* (2006.01)
(Continued)

(52) U.S. Cl.
CPC .............. *A61M 1/127* (2013.01); *A61M 1/1037* (2013.01); *A61M 1/1044* (2014.02); *A61M 1/122* (2014.02);
(Continued)

(58) Field of Classification Search
CPC ............ A61M 1/1006; A61M 1/1037; A61M 1/1044; A61M 1/127; A61M 1/122; A61F 2002/484–2002/487; A61F 2250/0012–2250/0013
USPC .......................................... 623/11.11, 24, 26
See application file for complete search history.

(56) References Cited

U.S. PATENT DOCUMENTS

| | | |
|---|---|---|
| 3,974,854 A | 8/1976 | Kurpanek |
| 2002/0022759 A1 | 2/2002 | Forsell |

(Continued)

FOREIGN PATENT DOCUMENTS

| | | |
|---|---|---|
| DE | 10353943 | 6/2005 |
| DE | 102007018797 A1 | 11/2007 |

(Continued)

OTHER PUBLICATIONS

International Search Report dated May 3, 2011 for PCT International application No. PCT/EP2011/054131.

(Continued)

*Primary Examiner* — Howie Matthews
(74) *Attorney, Agent, or Firm* — Ohlandt, Greeley, Ruggiero & Perle, L.L.P.

(57) ABSTRACT

A device for supplying energy to hydraulically or pneumatically actuated active implants. The device can take the form of pumping systems, metering systems, and/or occlusion systems. The device comprises a receiving coil for generating an electric voltage due to a changing magnetic flux that is generated by an extracorporeal transmitting coil. The receiving coil is designed such that said coil can be implanted into subcutaneous tissue. Furthermore, an electric line is provided for transmitting the electric current that is generated by the receiving coil from the receiving coil to the active implant. The device further comprises a compensation container for temporarily receiving a transmitter fluid, by means of which the active implant is activated. The compensating container is mounted on the receiving coil and/or on the electric line such that the compensating container together with the receiving coil and/or the electric line can be implanted into a common tissue or muscle pocket in the body of a patient.

10 Claims, 2 Drawing Sheets

(51) Int. Cl.
*A61F 2/00* (2006.01)
*A61M 5/142* (2006.01)
*A61M 5/145* (2006.01)
*A61N 1/378* (2006.01)

(52) U.S. Cl.
CPC .......... *A61F 2/0036* (2013.01); *A61M 5/14276* (2013.01); *A61M 2005/14513* (2013.01); *A61M 2205/8243* (2013.01); *A61N 1/3787* (2013.01)

(56) References Cited

U.S. PATENT DOCUMENTS

| | | |
|---|---|---|
| 2003/0019498 A1 | 1/2003 | Forsell |
| 2005/0107847 A1 | 5/2005 | Gruber et al. |
| 2006/0211914 A1 | 9/2006 | Hassler et al. |
| 2007/0264073 A1 | 11/2007 | Hanada et al. |

FOREIGN PATENT DOCUMENTS

| | | |
|---|---|---|
| DE | 102007048859 A1 | 4/2009 |
| DE | 102008018792 A1 | 10/2009 |
| WO | 0009049 | 2/2000 |

OTHER PUBLICATIONS

Written Opinion dated May 3, 2011 for PCT International application No. PCT/EP2011/054131.

English Translation of International Preliminary Report on Patentability dated Sep. 18, 2012 in corresponding International Application No. PCT/EP2011/054131.

English Translation of the Written Opinion of the International Search Authority dated Sep. 18, 2012 in corresponding International Application No. PCT/EP2011/054131.

DEVICE FOR SUPPLYING ENERGY TO HYDRAULICALLY OR PNEUMATICALLY ACTUATED ACTIVE IMPLANTS

BACKGROUND

1. Field of the Disclosure

The disclosure refers to a device for supplying energy to hydraulically or pneumatically actuated active implants.

2. Discussion of the Background Art

These may be pumping systems such as artificial hearts or cardiac assist systems (ventricular assist devices), metering systems (such as drug pumps for pain therapy) or occlusion systems (sphincters).

Ideally, such active implants should be configured so as to be fully implantable so that it becomes unnecessary to provide percutaneous energy lines for the supply of energy. One possible way of supplying energy is to supply current to the implant in a wireless manner via an inductive energy transmission unit. Here, implantable coils are used to transmit energy to the target implant, which implantable coils are most frequently implanted in the subcutaneous tissue of the abdominal section or the pectoral muscle area. Such an arrangement for wireless energy transmission is described, for example, in the German Patent Application DE 10 353 943.

For the purpose of volume compensation, hydraulically or pneumatically actuated active implants additionally use a so-called compliance or compensation chamber. This chamber serves to temporarily receive the transmitter fluid by which the active implant is operated.

For both the compensation chamber and the receiving coil, a pocket has to be prepared between the muscle layers or in the subcutaneous tissue so that these components can be implanted in this pocket. In practice, the number of components implanted substantially increases the risk of pocket infections. Moreover, the surgery and the sterilization are more time-consuming. Further, the comfort of wear for the patient is affected negatively.

It is also known to provide compensation containers on the outer wall of the implant, whereby the implant becomes bigger. Therefore, implantability may no longer be an option with small persons, such as children. Further, as a rule, a subcutaneous arrangement of such a device is out of question because of its structural size. Besides, compensation containers are known that are designed as flat bags. These bear an increased risk of pocket infections and are often perceived by patients as disturbing.

It is an object of the disclosure to provide a device for supplying energy to hydraulically or pneumatically actuated active implants that can be implanted in a patient's body in a simple and safe manner.

SUMMARY

A device for supplying energy to hydraulically or pneumatically actuated or active implants comprises a receiving coil for generating an electric voltage that is caused by a changing magnetic flux generated by an extracorporeal transmitting coil. The receiving coil is configured such that it is adapted to be implanted into subcutaneous tissue. The active implant may be a pumping system, in particular an artificial heart or a cardiac assist system (ventricular assist device) or, further, a metering system and/or a closing system.

The hydraulic or pneumatic actuation of the active implant is effected through a transmitter fluid.

An electric line is provided for the transmission of the electric current generated by the receiving coil from the receiving coil to the active implant. Further, the device comprises a compensation container for temporarily receiving a transmitter fluid by which the active implant is actuated.

According to the disclosure, the compensation container is arranged such on the receiving coil and/or the electric line that the compensation container is implantable in a tissue or muscle pocket in a patient's body together with the receiving coil and/or electric line. Preferably, the compensation container is arranged immediately on the receiving coil and/or the electric line.

The features mentioned above offer the advantage that the compensation container, the receiving coil and, possibly, the electric line can be implanted together in a single tissue or muscle pocket in a patient's body. Thereby, the process of implantation as such is simplified. Further, the risk of a pocket infection decreases and the comfort of wear for the patient is increased.

It is preferred that the receiving coil is flexible. The receiving coil may comprise further features that are described in the German Patent Application DE 10 353 943.

The device according to the disclosure allows for a compact structure so that the freedom of movement and the living quality of a patient are improved. Further, a faster ingrowth of the implanted device becomes possible.

According to the disclosure, in contrast with known systems, where the coil is placed inside a compensation container, a damping of the energy transmission by the surrounding liquid and thus a deterioration of the efficiency do not occur. Further, an exact positioning between the implanted receiving coil and the extracorporeal coil is still possible, which is not the case with known coils movably arranged in the compensation container. As such, a good coupling and thus a sufficient energy transmission can be achieved.

Preferably, the receiving coil and/or the compensation container are toroidal in shape.

The compensation container may be in the form of a hose, in particular with a flexible outer wall. The geometry and the wall thickness of the outer wall define the compliance properties, i.e. the resilience, of the chamber. A flexible design of the outer wall further makes it possible to avoid pressure peaks in the compensation chamber. Liquids or gases may be used as the transmitter fluid.

It is preferred that the compensation container and in particular the receiving coil and/or the electric line are arranged in an incompressible housing. The same may also be toroidally shaped, for example, and may moreover comprise a toroidal opening for the compensation container. Thereby, the compensation container is not exposed to the internal body pressure and to the pressure exerted by muscles possibly adjacent thereto. Thus, it is possible to avoid undesirable compression and high pressures in the compensation container. The incompressible housing further serves as protection from impacts and pressures that may act on the implanted device from outside the patient.

The incompressible housing may enclose the compensation container completely or may be open to the body of a patient, i.e. in a proximal direction, and may not enclose the compensation container in this direction. In any case, the incompressible housing provides protection from impacts and pressures acting on the patient from outside.

In a particularly preferred embodiment the incompressible housing is filled with a medium for adjusting the compliance of the outer wall of the compensation container. This medium surrounds the compensation container. The compliance is adjustable independent of the wall tension of the compensation container by changing the volume, the density and/or the compressibility of the medium in the incompressible housing. When a high pressure prevails in the cavity of the incompressible housing, the compliance is low, whereas it is high when a low pressure prevails. It is thus possible to adjust the mechanical properties, in particular the elasticity of the compensation container, by introducing different media into the cavity of the incompressible housing, without having to apply changes to the implanted device for this purpose. For this purpose it is preferred that the incompressible housing comprises an implantable port for supplying and draining the medium so that, via this port, the elasticity of the compensation container can be adjusted by supplying and draining a fluid with specific mechanical properties. Preferably, the port is arranged near the patient's skin such that it is easily accessible using a syringe. Such ports are known per se and are provided with a puncture surface adapted to be punctured by a syringe so that medium can be supplied or withdrawn in this manner. For the adjustment of the compliance of the outer wall of the compensation container by means of the medium in the incompressible housing, the incompressible housing must enclose the container completely.

The compensation container may also be provided with an implantable port for supplying or withdrawing the transmitter fluid, which is configured as explained above.

The port of the compensation container may be arranged immediately on the compensation container itself or it may be connected with the same via a connection hose. An arrangement immediately on the compensation container is reasonable if the housing of the compensation container is designed with such stability that it cannot be pierced by a syringe cannula. If, however, there is a risk of a flexible compensation container being punctured, the port may be connected with the compensation container via a connection hose so that a free positioning is possible. By allowing a supply or a withdrawal of the transmitter fluid, said port makes it possible to achieve a pre-stressing of the compensation container or to regulate the pressure in the compensation container. Both ports mentioned allow an optimal adjustment of the damping of the system, which is of utmost importance with cardiac assist systems.

Due to the flexible outer wall of the compensation container it is possible that the same buffers energy available in the active implant by building up an overpressure of the transmitter fluid and by stretching the outer wall of the compensation container. The principle of energy storage or energy buffering by the compensation container is analogous with the principle of energy storage in a plate capacitor in the field of electrical engineering. The energy available in the implant is buffered in the compensation container by using the transmitter fluid to build up an overpressure in this container by tensioning the outer wall of the compensation container. When needed, the energy stored can be released to the implant again. Here, the advantages are the low-loss storage and the prompt availability of the energy. Further, it is possible, following the same principle, to use the arrangement of the disclosure to effect a damping in hydraulic or pneumatic arrangements.

The storage of volume in the compensation container serves to temporarily receive or store the transmitter fluid required to actuate the active implant. The transmitter fluid can be displaced into the target implant by means of a pump. By a change in the volume of the target implant, the effects required from the implant are obtained (e.g. artificial muscle, drug delivery etc.).

With respect to the arrangement and the geometry of the compensation container, one should be careful not to affect the energy transmission properties. In particular, the compensation container is not arranged in the area between the implanted receiving coil and the extracorporeal induction coil so as to keep the distance between the two coils short and to avoid an adverse influence on energy coupling. However, the compensation container can be arranged proximally with respect to the receiving coil, i.e. in the adjacent portion of the body, without compromising the energy transmission properties.

In a preferred embodiment the compensation container is arranged concentrically with respect to the receiving coil in the radial direction on the inner or the outer edge of the coil.

As an alternative, the compensation container can be arranged in the free inner space in the radial direction within the receiving coil and may be disc-shaped, in particular.

Further, the compensation container may be arranged as a vessel in the region where the receiving coil is connected with the electric line.

Moreover, the compensation container may be arranged in parallel or coaxially with the electric line between the receiving coil and the active implant.

Further, it is possible to arrange the compensation container as a vessel in the region, where the active implant is connected with the electric line. The compensation container may also be arranged along the electric line between the receiving coil and the active implant.

Optional combinations of the latter arrangements are possible.

Instead of an incompressible chamber, it is also possible to provide a rigid flexible housing that allows for a better ingrowth in a patient's body. The housing is preferably designed such that the pressure buildup caused by the expansion of the compensation container does not deform the housing and does not result in an increase in the volume thereof. Nevertheless, the housing may be of a flexible design, for example by providing a multiple-element structure, such that its shape can adapt to the movements and to the body of a patient.

It is preferred that the compensation container and the receiving coil have no common intermediate wall.

It is further preferred that all materials of the device are suited for implantation into a patient's body.

The electric line for transmitting the electric current generated by the receiving coil to the active implant and the fluid line, via which the transmitter fluid can be conveyed from the compensation container to the active implant and back, are preferably arranged in a multiple-lumen hose, i.e. in a hose integrating several separate cannels for guiding wires and pressure media.

In another preferred embodiment both the compensation container and the receiving coil are toroidally shaped, with the receiving coil being arranged as a torus in a larger torus of the compensation container. The compensation container and the receiving coil are arranged coaxially in this case, the compensation container including the receiving coil. Preferably, support devices are provided that support the receiving coil such that it remains stationary, i.e. such that it does not move especially with respect to the implanted compensation container.

The following is a detailed description of preferred embodiments of the disclosure with reference to the drawing.

DETAILED DESCRIPTION OF THE PREFERRED EMBODIMENT

Figure 1:
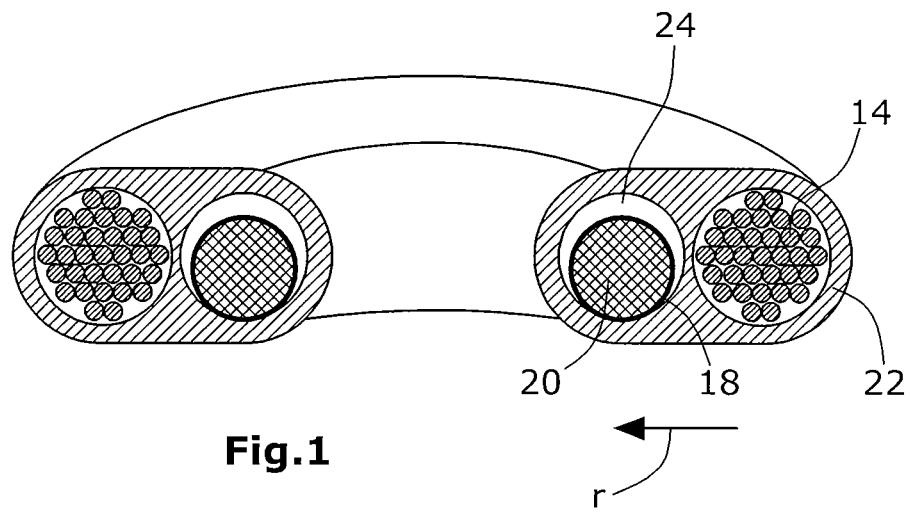
FIG. 1 shows a cross section of a receiving coil and a compensation container.

FIG. 1 shows the receiving coil 14 in section. The latter is arranged within the incompressible housing 22 which is toroidal in shape. The compensation container 18, which receives the transmitter fluid 20, extends in the radial direction inside the receiving coil 14. The medium 24 for adjusting the compliance of the outer wall of the compensation container 18 is arranged in the cavity between the outer wall of the compensation container 18 and the inner wall of the incompressible chamber 22. The same can be supplied to or withdrawn from the incompressible housing 22 via a non-illustrated port.

Figure 2:
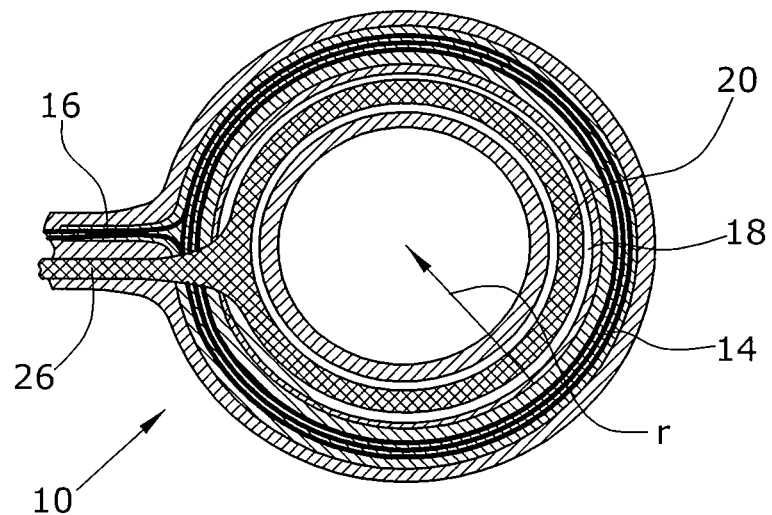
FIG. 2 is a schematic sectional view of the receiving coil and the compensation container in top plan view.

In addition to the components mentioned, FIG. 2 illustrates the electrical line 16 to the implant 12. Further, the fluid line 26 is shown via which the transmitter fluid 20 can be conveyed from the compensation container 18 to the active implant 12 and back. Here, conveying is effected by means of a non-illustrated pump which may have an electric drive, for instance.

Figure 3A:
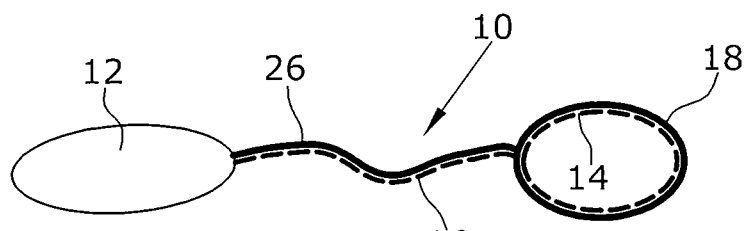
FIGS. 3a-3f are possible arrangements of the compensation container.
Figure 3B:
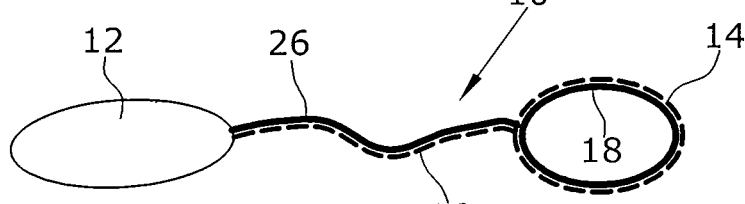

In FIGS. 3a-3f, different arrangements of the compensation container are shown. In FIG. 3a, the compensation container 18 is arranged concentrically with respect to the receiving coil 14 at the outer edge thereof. In contrast thereto, it is arranged at the inner edge of the receiving coil 14, again in a concentric manner.

Figure 3C:
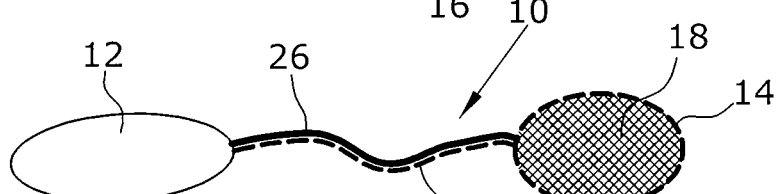

In FIG. 3c, the compensation container is arranged as a disc within the coil 14.

Figure 3D:
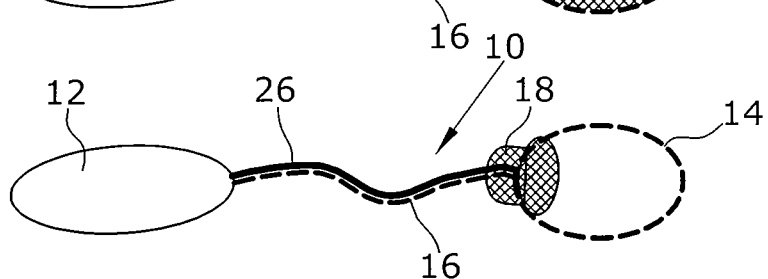

According to FIG. 3d, the compensation container 18 may also be arranged as a compact vessel in the region of the hub of the receiving coil 14, i.e. in the region where the receiving coil 14 is connected with the electric line 16.

Figure 3E:
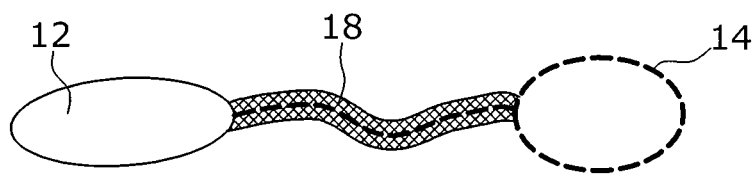

Further, according to FIG. 3e, the compensation container 18 may be arranged in parallel or coaxially with the electric line 16 between the receiving coil 14 and the active implant 12. Here, the compensation container may be in the form of a hose.

Figure 3F:
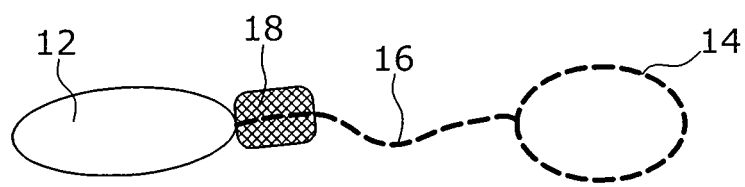

Further, as illustrated in FIG. 3f, the compensation container 18 may be arranged as a vessel in the region where the active implant 12 is connected with the electric line 16. In FIG. 3f, the compensation container 18 is arranged immediately at the active implant 12. It is also possible to arrange the compensation container 18 at an optional position along the electric line 16 between the receiving coil 14 and the active implant 12.

What is claimed is:

1. A device for supplying energy to a hydraulically or pneumatically actuated active implant, wherein hydraulic or pneumatic actuation of the active implant is effected via a transmitter fluid, and wherein the device comprises:
   a receiving coil for generating an electric voltage caused by a changing magnetic flux generated by an extracorporeal transmitter coil, the receiving coil being designed such that it is adapted for implantation in subcutaneous tissue,
   an electric line for transmitting electric current generated by the receiving coil from the receiving coil to the active implant, and
   a compensation container for temporarily storing the transmitter fluid via which the active implant is actuated,
   wherein the compensation container is arranged at the receiving coil and/or at the electric line such that the compensation container is adapted to be implanted, together with the receiving coil and/or the electric line, in a common tissue or muscle pocket in a patient's body,
   wherein the compensation container and the receiving coil are arranged in an incompressible housing, wherein the incompressible housing is filled with a medium for adjusting compliance of an outer wall of the compensation container, wherein the medium surrounds the compensation container, and
   wherein the compliance is adjustable independently of wall tension of the compensation container by changing a volume, a density and/or a compressibility of the medium in the incompressible housing.

2. The device of claim 1, wherein the compensation container is a hose with a flexible outer wall.

3. The device of claim 1, wherein the electric line is arranged in the incompressible housing.

4. The device of claim 1, wherein the incompressible housing fully encloses the compensation container.

5. The device of claim 1, wherein the outer wall of the compensation container comprises a flexible outer wall so that energy available in the active implant can be stored in the compensation container by building up an overpressure of the transmitter fluid in the compensation container and by tensioning the outer wall of the compensation container, and wherein the compensation container further acts as a damping element.

6. The device of claim 1, wherein the compensation container is arranged concentrically with respect to the receiving coil in the radial direction or on an inner edge or an outer edge of the receiving coil.

7. The device of claim 1, wherein the compensation container is arranged in an inner space in a radial direction within the receiving coil.

8. The device of claim 1, wherein the compensation container is arranged as a vessel in an area where the receiving coil is connected with the electric line.

9. The device of claim 1, wherein the compensation container is adapted to be arranged between the receiving coil and the active implant in a manner parallel or coaxial with the electric line.

10. The device of claim 1, wherein the compensation container is adapted to be arranged as a vessel in an area where the active implant is connected with the electric line and/or is adapted to be arranged along the electric line between the receiving coil and the active implant.

* * * * *